United States Patent [19]

Chang

[11] Patent Number: 5,063,054

[45] Date of Patent: Nov. 5, 1991

[54] MICROBIAL PRODUCTS USED FOR TREATMENT OF HEPATITIS

[76] Inventor: Joseph Chang, 6-21-3 Sieji, Setagaya-ku, Tokyo, Japan

[21] Appl. No.: 512,053

[22] Filed: Apr. 19, 1990

Related U.S. Application Data

[63] Continuation of Ser. No. 182,943, Apr. 18, 1988, abandoned.

[51] Int. Cl.$^5$ ............................................. A61K 35/74
[52] U.S. Cl. ...................................... 424/92; 424/520; 424/195.1; 435/824
[58] Field of Search ...................... 424/520, 195.1, 92; 435/824

[56] References Cited

U.S. PATENT DOCUMENTS

| | | | |
|---|---|---|---|
| 3,836,648 | 9/1974 | Chang | 424/92 |
| 3,857,935 | 12/1974 | Chang | 424/95 |
| 4,663,160 | 5/1987 | Tsay et al. | 424/92 |
| 4,693,891 | 9/1987 | Collins et al. | 424/92 |
| 4,755,382 | 7/1988 | Flaherty | 514/885 |

FOREIGN PATENT DOCUMENTS

| | | |
|---|---|---|
| 915106 | 11/1972 | Canada . |
| 7000679 | 1/1970 | Japan . |
| 1254948 | 11/1971 | United Kingdom . |

*Primary Examiner*—Douglas W. Robinson
*Assistant Examiner*—Jean C. Witz
*Attorney, Agent, or Firm*—Ostrolenk, Faber, Gerb & Soffen

[57] ABSTRACT

A water soluble and ethanol insoluble extract of microbial product obtained by the cultivation of *Achromobacter stenohalis* is used to combat viral diseases.

5 Claims, No Drawings

MICROBIAL PRODUCTS USED FOR TREATMENT OF HEPATITIS

This is a continuation of application Ser. No. 182,943, filed on Apr. 18, 1988, abandoned.

BACKGROUND OF THE INVENTION

In my Canadian Patent 915,106, I described a microbial product derived from *Achromobacter stenohalis* which had antiviral activities with a treatment of Myxovirus such as pup's distemper and was capable of suppressing the growth of tumors. The product was produced by cultivating the bacterium in a saline solution. This product has been used commercially in Japan for many years with great success. With respect to parvoviral enteritis in puppies and panleucopenia in cats, in cure rates in the range of 60–70% were achieved when the microbial product was administered for one week or more.

Some published studies on the use of the microbial product of the Canadian patent can be found in Okuda, Studies on the Treatment of Canine Distemper-Like Disease With Domon, Jui Chikusan Shimpo (Journal of Veterinary Medicine) (Tokyo), No. 482:1217–1219; Id. No. 495:545–550; Shibani et al., Studies on the Treatment of Canine Distemper with Domon-L, Jui Chikusan Shimpo, No. 498:725–729; Samejima et al., Experiment on the Antibody Response of Dogs Injected With Distemper Live Vaccine to Administration With Domon-L; and Kajiyama et al., Studies on the Treatment of Canine Distemper With Domon-L, Jui Chikusan Shimpo, No. 500:8–11. It has been theorized that the product may stimulate the production of a neutralizing antibody or may possess activity as an interferon inducer.

It has now been discovered that a water soluble, ethanol insoluble extract fraction of the microbial product of the Canadian patent exhibits a greater spectrum of activity. For example, cure rates for puppies' parvoviral enteritis and feline panleucopenia of 100% have been obtained with the administration of the new extract for three days or less. It has been found useful in the treatment of human hepatitis.

It is accordingly the object of this invention to provide a new microbial product which is useful for the treatment of viral infections in man and animals. This and other objects of the invention will become apparent to those of ordinary skill in this art from the following detailed description.

SUMMARY OF THE INVENTION

This invention relates to a microbial product derived from a strain of *Achromobacter stenohalis* which product is water soluble and ethanol insoluble and to the use thereof in treating viral infections.

DESCRIPTION OF THE INVENTION

The bacterium *Achromobacter stenohalis*, from which the microbial product of this invention is derived, has been isolated from seawater, marine mud and marine phytoplankten. A preferred strain is ATCC 21710. The identity of the *Achromobacter stenohalis* is described in detail in my aforementioned Canadian patent.

The cultivation of the bacterium can be carried out as set forth in my aforementioned Canadian patent. Thus, the *Achromobacter stenohalis* is cultivated in a saline medium which may contain, optionally, a nutrient such as glucose and pepton. While I previously preferred a salt concentration of 1.5 to 2.5%, and incubation at 25°–36° C. for 24–48 hours, I now preferred to use about 3.5% salt solution and one hour of incubation at a higher temperature of about 56° C. Nevertheless, the general conditions which I described in my prior patent can be used if so desired.

The use of a freeze-thaw cycle to remove slime from the culture broth described in my prior patent can be used but I now prefer simply to subject the broth to sonification, separate the precipitate from the supernatant and subject the supernatant to dialysis against distilled water. After filtering off any remaining sediment, the dialyzed supernatant can be lypholized if desired or it can be directly subjected to the extraction procedure.

To prepare the liquid for the extraction, it is first subjected to a low-speed centrifuge (up to 7,500 rpm and preferably about 5,000 rpm), the precipitate and supernatant separated, the supernatant subjected to a high-speed centrifuge (above 9,000 rpm and preferably about 12,000 rpm) and the supernatant and precipitate separated. Centrifugation periods of 15 to 60 minutes are normally used. The high-speed centrifuge precipitate can, if desired, be washed with water and is then subjected to the well-known Westphal's phenol extraction.

In the phenol-water extraction, the bacterial precipitate is suspended in water at about 50° to 70° C., 90% phenol at the same temperature is added with vigorous stirring and then the mixture is maintained at elevated temperatures for a period of time. I prefer to effect the mixing at about 55° C. for 30 minutes followed by adding an equal volume of water and then maintaining the mixture in 60° for an additional 30 minutes. The mixture is cooled to ambient temperature followed by separating the phenol and water, for example by subjecting the mixture to centrifugation. The water extract is dialyzed against distilled water to remove traces of phenol and small amounts of low molecular weight bacterial substances. An RNA-free extract is prepared by] subjecting the dialyzed water extract to RNase followed by three courses of very high-speed centrifugation (preferably 100,000 g) for three hours.

The precipitate is then suspended in a salt solution, for example 0.5M NaCl which is mixed with ethanol, preferably at a weight of 1:10 and 1:20 maintained at about 4° C. for one or two hours. The mixture is subjected to low speed centrifugation, the resulting precipitate separated from the supernatant and suspended in water and dialyzed against distilled water. The resulting water soluble, ethanol insoluble extract can be used as is or, if desired, can be lypholized.

The microbial extraction products of the present invention can be used for preparing suitable therapeutic compositions in any form suitable for their application as is well known in the art. While the particular dosage is best determined by the attending clinician or veterinarian, in general the therapeutic dose will be in the range of about 5–350, preferably about 6–320 microgram of extract per kilogram host body weight.

In order to demonstrate the enhanced activity of the extract of the present invention compared to the microbial product of my Canadian patent, a therapeutic composition was prepared by dissolving one milligram of the product in one ml. of dissolved water and inoculating puppies suffering with parvoviral enteritis and cats suffering with feline panleucopenia once per day, subcutaneously, with a dosage of 1 ml of the solution. The results were set forth in the following tables.

TABLE NO. 1

Hemmorrhagic entritis of Puppies

| NO. | SEX | AGE | TEMPERATURE | SYMPTOMS DIARRHEA | EMESIS | WBC | TREATED TIMES | PROGNOSIS |
|---|---|---|---|---|---|---|---|---|
| 1 | M | 3 yrs. | 39.5° C. | **** | *** | 2600 | 5 | cure |
| 2 | F | 2 yrs. | 40.2° C. | **** | **** | 2200 | 4 | cure |
| 3 | M | 1 yr. | 40.5° C. | **** | **** | 2600 | 4 | cure |
| 4 | F | 1 yr. | 40.5° C. | **** | *** | 5200 | 4 | cure |
| 5 | F | 1 yr. | 40.8° C. | **** | **** | 4200 | 4 | cure |
| 6 | F | 4 yrs. | 40.0° C. | **** | **** | 5300 | 5 | cure |
| 7 | M | 3 yrs. | 40.7° C. | **** | **** | 4300 | 4 | cure |
| 8 | F | 1 yr. | 41.0° C. | **** | **** | 4600 | 3 | cure |
| 9 | M | 4 mos. | 40.0° C. | **** | **** | 5000 | 5 | cure |
| 10 | F | 2 yrs. | 39.1° C. | **** | **** | 3300 | 4 | cure |
| 11 | M | 2 yrs. | 39.8° C. | **** | **** | 2200 | 4 | cure |
| 12 | F | 10 yrs. | 40.3° C. | **** | **** | 4200 | 4 | cure |
| 13 | F | 7 yrs. | 39.0° C. | **** | **** | 4000 | 2 | cure |
| 14 | M | 5 mos. | 40.3–40.8° C. | **** | **** | 3400–3800 | 5 | cure |
| 15 | F | 1.5 yrs. | 40.3° C. | **** | **** | 5500 | 5 | cure |
| 16 | F | 2 yrs. | 40.7° C. | **** | **** | 6200 | 4 | cure |
| 17 | M | 1 yr. | 40.0° C. | **** | **** | 5100 | 4 | cure |
| 18 | F | 14 yrs. | 40.6° C. | **** | **** | 7400 | 4 | cure |
| 19 | F | 4 yrs. | 39.5° C. | **** | **** | 2800 | 6 | cure |
| 20 | F | 2 yrs. | 41.0° C. | **** | **** | 4500 | 4 | cure |
| 21 | M | 5 yrs. | 39.7° C. | **** | **** | 5000 | 7 | cure |
| 22 | M | 4 yrs. | 39.9° C. | **** | *** | 6200 | 4 | cure |
| 23 | M | 5 yrs. | 39.5° C. | **** | *** | 5000 | 7 | cure |
| 24 | F | 1 yr. | 40.1° C. | **** | **** | 7000 | 4 | cure |
| 25 | M | 8 yrs. | 41.0° C. | **** | **** | 3800 | 5 | cure |

TABLE NO. 2

Feline FPL (Feline Panleukopenia)

| NO. | SEX | AGE | TEMPERATURE | SYMPTOMS DIARRHEA | EMESIS | WBC | TREATED METHOD | TREATED TIMES | PROGNOSIS |
|---|---|---|---|---|---|---|---|---|---|
| 1 | M | 1 yr. | 40.0° C. | **** | **** | 2400 | LPS 0.5 ml, 100 ml, ABPC. | 4 | cure |
| 2 | M | 1 yr. | 40.0° C. | **** | **** | 4200 | LPS 0.5 ml, 100 ml, ABPC. | 5 | cure |
| 3 | M | 4 yrs. | 40.0° C. | **** | **** | 6000 | LPS 0.5 ml, 100 ml, ABPC. | 1 | cure |
| 4 | F | 7 yrs. | 40.0° C. | **** | **** | 2700 | LPS 0.5 ml, 100 ml, ABPC. | 2 | cure |
| 5 | M | 1 yr. | 40.0° C. | **** | **** | 1200 | LPS 0.5 ml, 100 ml, ABPC. | 3 | cure |
| 6 | M | 3 yrs. | 39.5° C. | **** | **** | 1800 | LPS 0.5 ml, 100 ml, ABPC. | 5 | cure |
| 7 | F | 3 yrs. | 39.2° C. | **** | **** | 3100 | LPS 0.5 ml, 100 ml, ABPC. | 2 | cure |
| 8 | F | 5 mos. | 40.0° C. | **** | **** | 2700 | LPS 0.5 ml, 100 ml, ABPC. | 4 | cure |
| 9 | M | 1 yr. | 40.3° C. | **** | **** | 4100 | LPS 0.5 ml, 100 ml, ABPC. | 4 | cure |
| 10 | M | 3 yrs. | 39.3° C. | **** | **** | 6800 | LPS 0.5 ml, 100 ml, ABPC. | 5 | cure |
| 11 | F | 1 yr. | 39.7° C. | **** | **** | 4100 | LPS 0.5 ml, 100 ml, ABPC. | 3 | cure |

In a clinical demonstration, 60 cases of acute viral hepatitis (Type A—16 cases onset seven to ten days; Type Non-A, Non-B—14 cases; Type B—30 cases onset two to three weeks) were treated by a double blind technique receiving injections of 1 ml. of physiological saline either with or without 0.5 mg. of the product. For Type A, the dosage schedule was one injection per day for the first week and then one injection every other day for the following two weeks. For Type B, the dosage schedule was once a day for eight weeks. The clinical symptoms were a general malaise, anorexia, icterus and dyspepsia and the diagnosis was confirmed by laboratory tests. For the Type A patients, all clinical symptoms disappeared after two weeks of treatment and hepatomegaly became normal after three weeks of treatment. The control group for Type A hepatitis began to recover little by little after the fourth week of treatment. The six cases of Non-A-Non-B treated with the product became normal after two to three weeks of treatment while in the control group, seven recovered after 5 weeks of treatment and the remaining member recovered after the sixth week of treatment. With respect to the Type B hepatitis, fourteen of the product treated patients had lost all clinical symptomology after three weeks of treatment and the remaining case took five weeks while the control group had ten members which eliminated the clinical symptoms as late as five weeks after treatment and one which did not lose the clinical symptoms after the eight weeks of treatment. With regard to the liver function, the time required for the SGPT to become normal is set forth in the following table.

| Cases | | 2 weeks | 3 weeks | 3 to 5 weeks | More than 5 weeks |
|---|---|---|---|---|---|
| PRODUCT | | | | | |
| Type A | 4 | 2 | 2 | 0 | 0 |
| NANB | 6 | 1 | 1 | 4 | 0 |
| Type B | 15 | 4 | 5 | 6 | 0 |
| Total | 25 | 7 | 8 | 10 | 0 |
| CONTROL | | | | | |
| Type A | 12 | 0 | 2 | 7 | 3 |
| NANB | 8 | 0 | 3 | 3 | 2 |
| Type B | 15 | 1 | 3 | 12 | 9 |
| Total | 35 | 1 | 8 | 12 | 14 |

Various changes and modifications can be made in the invention described above without departing from the spirit and scope of the invention. The embodiments described herein were set forth for the purpose of illustration only.

What is claimed is:

1. A method of treating human hepatitis which comprises administering to a human in need thereof a therapeutically effective amount of an agent which comprises a water soluble, ethanol insoluble extract derived from cells of *Achromobacter stenohalis*.

2. The method of claim 1, wherein the agent is administered by injection.

3. The method of claim 1, wherein the hepatitis is type A.

4. The method of claim 1, wherein the hepatitis is type B.

5. The method of claim 1, wherein the hepatitis is type non-A, non-B.

* * * * *